United States Patent
Dorsel et al.

(10) Patent No.: US 6,320,196 B1
(45) Date of Patent: Nov. 20, 2001

(54) MULTICHANNEL HIGH DYNAMIC RANGE SCANNER

(75) Inventors: Andreas N. Dorsel, Menlo Park; Charles Z. Hotz, San Mateo, both of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/238,482

(22) Filed: Jan. 28, 1999

(51) Int. Cl.⁷ .................................................. G01N 21/64
(52) U.S. Cl. ...................... 250/458.1; 250/459.1
(58) Field of Search ............................ 250/458.1, 459.1, 250/461.1, 461.2

(56) References Cited

U.S. PATENT DOCUMENTS

| | | |
|---|---|---|
| 4,087,685 | 5/1978 | Froot . |
| 4,131,800 * | 12/1978 | Bruck et al. ...................... 250/461.2 |
| 4,243,318 | 1/1981 | Stöhr ...................................... 356/39 |
| 4,419,583 | 12/1983 | Noeller ............................. 250/458.1 |
| 4,490,040 | 12/1984 | Lucht et al. ......................... 356/318 |
| 4,573,796 | 3/1986 | Martin et al. ....................... 356/318 |
| 4,609,286 | 9/1986 | Sage, Jr. .................................. 356/73 |
| 4,816,687 | 3/1989 | Fehrenbach et al. ............. 250/459.1 |
| 5,022,757 | 6/1991 | Modell . |
| 5,091,652 | 2/1992 | Mathies et al. . |
| 5,143,854 | 9/1992 | Pirrung et al. . |
| 5,294,799 | 3/1994 | Aslund et al. .................... 250/458.1 |
| 5,304,810 * | 4/1994 | Amos ................................ 250/458.1 |
| 5,319,209 | 6/1994 | Miyakawa et al. ............... 250/459.1 |
| 5,324,401 | 6/1994 | Yeung et al. ...................... 204/180.1 |
| 5,381,224 | 1/1995 | Dixon et al. . |
| 5,418,371 | 5/1995 | Aslund et al. .................... 250/458.1 |
| 5,491,343 | 2/1996 | Brooker ............................ 250/458.1 |
| 5,491,344 | 2/1996 | Kenny et al. ..................... 250/461.1 |
| 5,498,875 | 3/1996 | Obremski et al. ................ 250/458.1 |
| 5,528,045 | 6/1996 | Hoffman et al. .................. 250/458.1 |
| 5,532,873 | 7/1996 | Dixon . |
| 5,631,734 | 5/1997 | Stern et al. . |
| 5,646,411 | 7/1997 | Kain et al. . |
| 5,682,038 | 10/1997 | Hoffman .......................... 250/458.1 |
| 5,736,410 | 4/1998 | Zarling et al. ....................... 436/172 |
| 5,760,951 | 6/1998 | Dixon et al. . |
| 5,837,475 | 11/1998 | Dorsel et al. . |
| 5,847,400 | 12/1998 | Kain et al. . |
| 5,991,030 * | 11/1999 | Yamamoto et al. ................. 356/346 |
| 6,043,506 * | 3/2000 | Heffelfinger et al. ............... 250/584 |

FOREIGN PATENT DOCUMENTS

| | | | |
|---|---|---|---|
| 0285170A2 | 10/1988 | (EP) | ............................. G01N/21/64 |
| 0440342A2 | 8/1991 | (EP) | ............................. G01N/21/64 |
| 01-148946 | 6/1989 | (JP) | ............................. G01N/21/64 |
| 02-269936 | 11/1990 | (JP) | ............................. G01N/21/64 |

* cited by examiner

*Primary Examiner*—Constantine Hannaher
(74) *Attorney, Agent, or Firm*—Gordon M. Stewart

(57) ABSTRACT

A method and apparatus for reducing the crosstalk between two or more dye channels in a multiple frequency laser induced fluorescence scanner in which two laser beams and associated optics are employed for focusing the two laser beams on a plurality of spatially separated spots, and for collecting and measuring the resulting emission from the sample labeled with at least two dyes. Crosstalk of the dye emission is minimized as the separated spots provide for a more nearly diagonal transformation matrix between signal channels and dye channels.

13 Claims, 4 Drawing Sheets

MULTICHANNEL HIGH DYNAMIC RANGE SCANNER

FIELD OF THE INVENTION

The present invention relates to a laser induced fluorescence scanner for DNA analysis and, more particularly, to a method and apparatus for minimizing crosstalk between dye channels in a multifrequency confocal microscope system.

BACKGROUND OF THE INVENTION

Pharmaceutical, biotechnology, or genomics companies use DNA analysis systems for target identification and drug screening in pharmaceutical drug discovery. In many of these systems, biomolecules (e.g. DNA, RNA, cDNA, Proteins) labeled with various dyes hybridize to chips that offer different molecular counterparts for hybridization of e.g. single stranded RNA in different areas of the chip. A scanner is then used to read the fluorescence of these molecules under illumination with suitable (most often laser) light. The scanner acts like a large field fluorescence microscope in which the fluorescent pattern caused by hybridization of labeled molecules is scanned on the chip. In particular, a laser induced fluorescence scanner provides for analyzing large numbers of genes/mutations/alleles in a biological sample. For various reasons it is often desirable to have samples labeled with different dyes hybridize (competitively) to the same chip or "sample carrier". In this case, a scanner needs to be able to be able to differentiate between the different kinds of molecules with as little crosstalk as possible.

U.S. Pat. No. 5,091,652 entitled "Laser Excited Confocal Microscope Fluorescence Scanner and Method" teaches a scanner for sequentially scanning the fluorescence from a series of labeled samples on a sample carrier with a confocal microscope. A single laser is employed for illuminating a single volume of a gel sample carrier and for receiving and processing fluorescence emissions from the volume to provide a display of the separated sample.

The Hewlett-Packard G2500A is a fluorescence scanner that employs a single laser with two filters for sequential multiple frequency scanning of fluorescently labeled chips in which two dyes may be applied to the sample. Crosstalk between the emission spectra from the two dyes reduces the signal to noise ratio of any detected signal. In particular. if the signal from one dye is very strong and the signal from the other dye is very weak, crosstalk between the two channels may severely limit the performance of a given system. While crosstalk can be reduced in some instances by first scanning with one laser and then illuminating the sample with another laser, the sequential registration of two full scans increases scan time to almost twice that of existing systems.

U.S. Pat. No. 5,294,799 discloses a microfluorometer which simultaneously excites one or more fluorophores with two or more wavelengths. The intensity of the excitation at each wavelength is time modulated at a separate frequency and a separate frequency-locked phase sensitive detector for each modulation frequency allows discrimination of the contribution from the individual spectra corresponding to each fluorophore. However. amplitude modulation at its best (i.e. for 100% contrast), results in a 50% reduction of the average laser power incident on the spot to be measured. This degrades signal performance either by increased shot noise or by increased saturation of the dye molecules at the peak of the modulation cycle. It may also result in the need for a more powerful laser source which is likely to increase cost.

The Scanarray 3000 scanner manufactured by the General Scanning Corporation and the Avalanche scanner manufactured by the Molecular Dynamics company each employ two lasers that are used to sequentially scan a chip that results in rather long scan times limiting throughput in many applications.

There exists a need for a laser induced scanner that can quickly determine the ratio(s) of the signals caused by two or more dyes. A need also exists to do such an analysis over a very wide dynamic range of that ratio (e.g. to a range up to going from 1:10000 to 10000:1) with a defined minimum signal-to-noise ratio of the ratio measurement.

It would be desirable and of considerable advantage to provide a multiple frequency scanner that differs from those employed in the prior art by reducing both crosstalk and scan time.

SUMMARY OF THE INVENTION

The present invention provides a method and apparatus for reducing the crosstalk between two or more dye channels in a multiple frequency laser induced fluorescence scanner while minimizing increases in cost or scan time. According to the invention, optics are employed for focusing the output of two lasers onto two spatially separated spots of a labeled sample, the resulting excitation and emission is collected and transmitted through the optics to detectors for measurement.

Cross-talk is reduced by the combination of one or more of the following techniques:

Using two lasers of different wavelengths to simultaneously excite the dye molecules of two spatially separated spots, and imaging the resulting emission onto two detectors through two different pinholes in a confocal arrangement such that the first detector only receives the emission resulting from the first laser and the second detector only receives the emission resulting from the second laser. Each of these detectors may also have filters to further limit detection to desired wavelengths only.

Replacing the pinholes with optical fibers (such fibers provide the added convenience of allowing placement of detectors in areas where the risk of picking up electronic noise is comparatively low).

Additional spectral separation of the signals from each laser spot through the use of a combination of filters, prisms, gratings and arrangements of apertures or detector arrays to separate the signals from different dyes, especially in systems that detect many photons per dye molecule. This may be used to either differentiate more than one dye within each laser spot (e.g. Cy 3 and Cy 3.5 in a spot illuminated with 532 nm radiation) or for other purposes (e.g. testing for spectral changes caused by chemical, thermal or other processes).

Exciting up, to two dyes with orthogonal polarizations of light to take advantage of the fact that many dyes exhibit the absorption characteristics of a linear dipole with re-emission of fluorescence occurring from a(n almost) parallel dipole. In the absence of depolarization effects (like relevant rotation of the molecules within the fluorescence decay time) exciting up to two dyes with orthogonal polarizations could be used to preferentially detect fluorescence that is polarized parallel to the excitation light of a given dye. In a four dye system this could be done with each of two pairs of two dyes for further reduction of crosstalk. In this case, a polarizer is introduced into each of the detection paths, the crosstalk between which is to be reduced by polarization. The polarizer is then oriented in such a way as to maximize transmission of the (partially) polarized emission to be detected in the channel in question.

Other aspects and advantages of the present invention will become apparent from the following detailed description, taken in conjunction with the accompanying drawings, illustrating by way of example the principles of the invention.

DETAILED DESCRIPTION OF THE PREFERRED EMBODIMENTS

The present invention provides a method and apparatus for reducing the crosstalk between two dye channels in a multiple frequency laser induced fluorescence scanner in which two laser beams are employed for illuminating a sample at two separated spots at two different wavelengths to differentiate between the two dyes. Two detectors detect the emission signals in the two channels.

In particular, the invention uses two different excitation wavelength ranges for differentiating between the resulting emission signals from the two dyes. These emission signals can be mathematically described (neglecting noise) by using a 2- element vector representing the two dye surface densities. Another 2-element vector may be employed for describing the two dye channel signals. The vector describing the dye surface densities multiplied by a 2×2 matrix yields the vector describing the detected emission signals. For an ideal system, this matrix is diagonal (or its permutation, in which case it is made diagonal by swapping the elements of one of the two vectors). In an actual system, there will always be finite-size off-diagonal elements that represent cross-talk. Given the quantum nature of light, every light signal is accompanied by shot noise. While for non-quantized signals, the inverse matrix would allow a perfect reconstruction of the dye concentrations, for a quantized system, the noise can be transferred from one channel into the other. For large ratios between the two signals, the noise caused by cross-talk may be bigger than the noise caused by the signal primarily associated with a given channel. This results in an increase of the detection limit and thus degrades system performance to a possibly unacceptable level.

The preferred embodiment of the invention is a multiple frequency scanner comprising one or more of the following four features:

1. Selecting dyes that have little overlap of their absorption and emission spectra.
2. Selecting detection filters for each dye that block signal from the other dye as far as possible without degrading signal from the dye to be detected.
3. Illuminating each dye in a spatially separated spot with a light wavelength that results in strong preferential excitation over the other dye. The spatial separation being larger than the spot diameter but smaller than the scan area.
4. Confocally imaging each of these excitation locations through a separate pinhole or a fiber acting among other functions as a pinhole to a detector.

Figure 1:
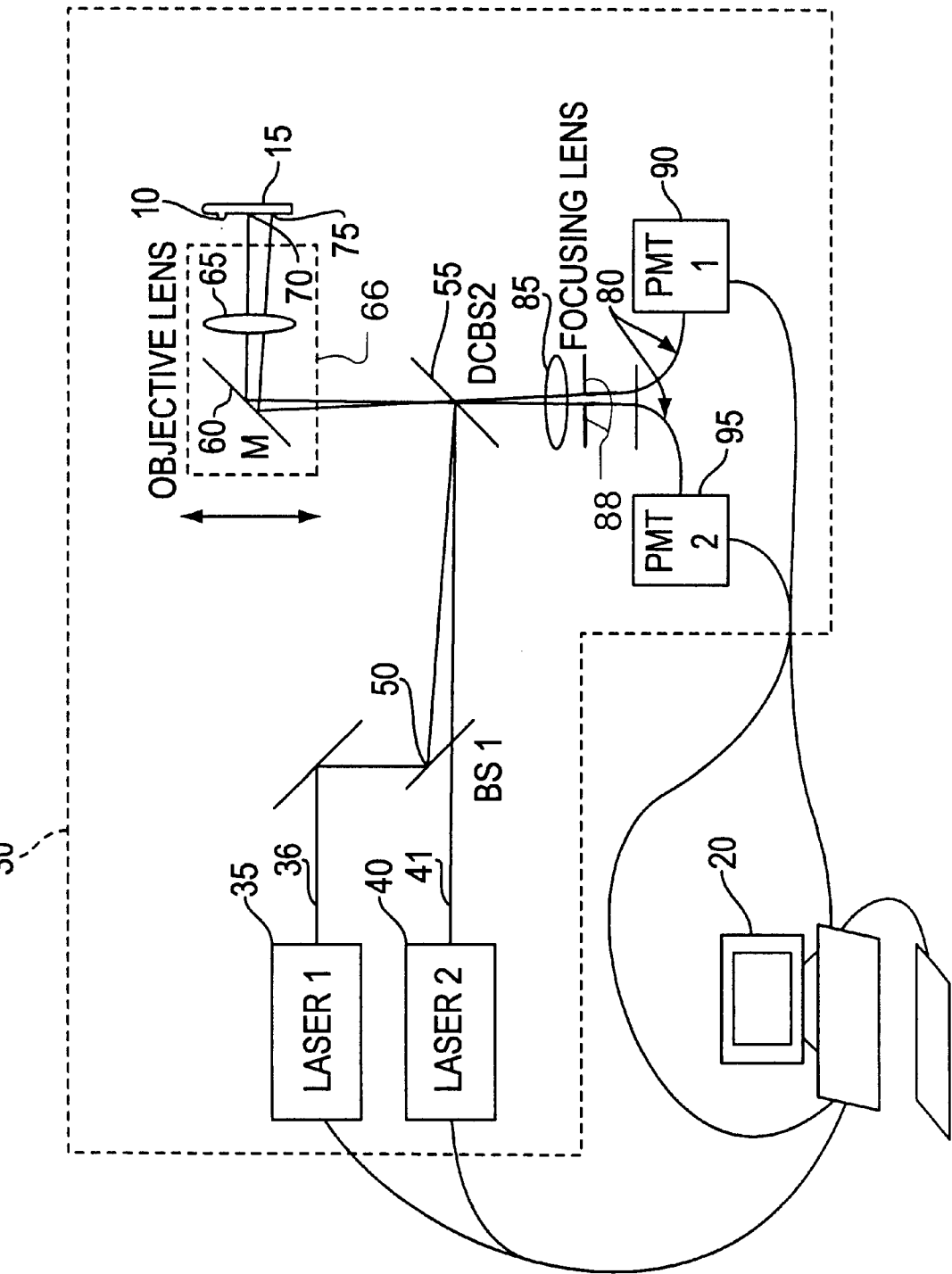
FIG. 1 is a simplified schematic representation of the preferred embodiment of the invention.

FIG. 1 is a simplified view of a confocal instrument system according to the present invention that allows an operator to simultaneously scan the multifrequency wavelength emission from two separated spots on a sample 10 labeled with two dyes and supported on a sample substrate 15. A computer 20, controls a laser induced fluorescence scanner 30. Detectors 90, 95 measure the emission resulting from the two spots.

As depicted further in FIG. 1, the preferred embodiment of the invention includes two lasers, 35, 40 which generate laser beams 36, 41 of different wavelengths for exciting two spots 70, 75 on the sample substrate 15. The laser beams 36, 41 are combined by passing them through a first (dichroic) beam splitter 50 at a slight angle (the illustration is exaggerated for clarity) and reflected off a dichroic beam splitter 55. The laser beams are redirected by a folding mirror 60 and focused by an objective lens 65 onto the two separate spots 70, 75. Fluorescent light emission from these spots is imaged back through the objective lens 65 and the fold mirror 60 and through dichroic beam splitter 55 for imaging onto two multi-mode (or in other instances monomode) fibers 80 by a focusing lens 85. Each fiber 80, one for each of the two spots' images, serves as a pinhole and also guides the fluorescent light emission to two respective detectors 90, 95. In the preferred embodiment, the detectors 90, 95 include photo multiplier tubes (PMT), but other devices such as an avalanche photo diode, a pin diode, a CCD-like structure, may be employed. The detectors 90, 95 may optionally contain a (compound) lens for imaging the light from the fiber onto the detector, as well as a filter for controlling the portion of the spectrum that is actually detected.

"The scanner may further include polarizers 88 each in a corresponding detection path, as shown in FIG. 1."

In a typical arrangement, the invention includes a chip for supporting a sample. the chip being scanned by moving the scan lens and fold mirror assembly 66 (FIG. 1) back and forth across the chip in one dimension, and slowly moving the chip in the orthogonal direction, for a two dimensional scan. If the two spots 70. 75 are then offset from each other by 100 microns in the slow scan direction, the total scan time only has to increase by 0.5 for both spots to cover the entire field of view. Sequential scanning systems would require an approximately twofold increase in scan time. By an appropriate choice of the sequence in which different dyes are excited (e.g. starting with the longest excitation wavelength) the impact of unintended bleaching is minimized.

In any of these designs, the scanner provides for low limit detection and ratio determination of two dye channels over a wide dynamic range. The invention also provides for two dye simultaneous reading and deconvolution (option for four dyes in simultaneous scans).

The order of the components in the foregoing described optical system may be changed by one of ordinary skill in the art without departing from the invention. For example, an optical system comprising a dichroic beam splitter for first splitting the fluorescent light into two channels, lenses (with possibly less demanding chromatic correction) for focusing the light of these two channels into two pinholes/fibers, wherein the fibers guide the light to PMT's with or without additional converging/collimating/imaging lenses.

As another example, the first dichroic used above to combine the two laser beams can be replaced with a mirror because the beams may be spatially separated due to their tilt.

Figure 2:
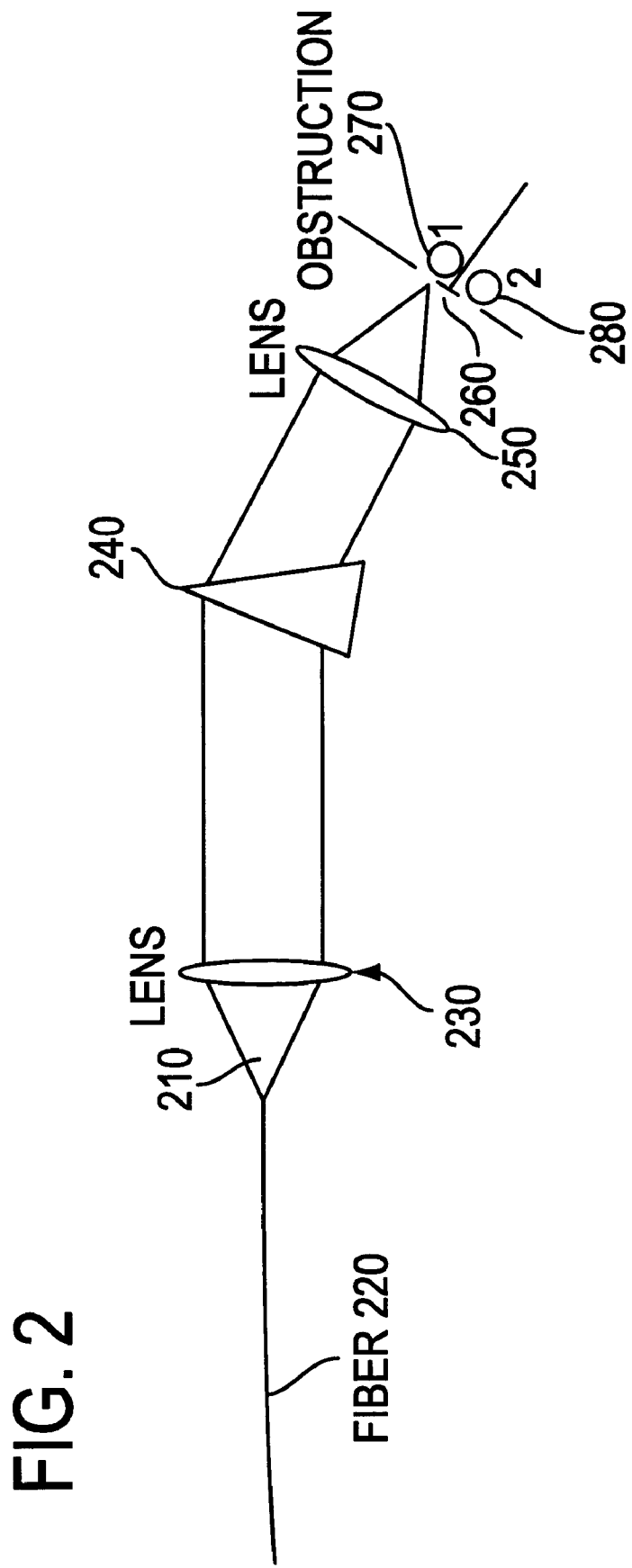
FIG. 2 depicts and alternative embodiment of part of the scanner portion of the invention illustrated in FIG. 1.

FIG. 2 shows a second embodiment for spectral analysis of the fluorescent light emission from a labeled sample. The light 210 exiting the fiber 220 is collimated by a lens 230, redirected by a dispersion device 240 such as a prism, and focused by another lens 250. Dispersion in the device 240 will generate a spectral distribution in the focal plane of this second lens. By using suitable obstructions, or apertures 260, it is possible to selectively direct different portions of this spectrum onto different detectors 270, 280. Alternatively, a holographic grating may be used for dispersion instead of a prism and it could be designed to eliminate the need for collimating and focusing lenses. In another embodiment, a linear or two-dimensional detector array (e.g. a CCD) can be used to act both as a set of detectors and provide the function of obstruction with apertures by virtue of the geometry of the different photosensitive areas on it. Alternatively. the lenses may be replaced with mirrors, and instead of an obstruction, a set of waveguides or fibers may be used to redirect different portions of the spectrum to different detectors.

Figure 3:
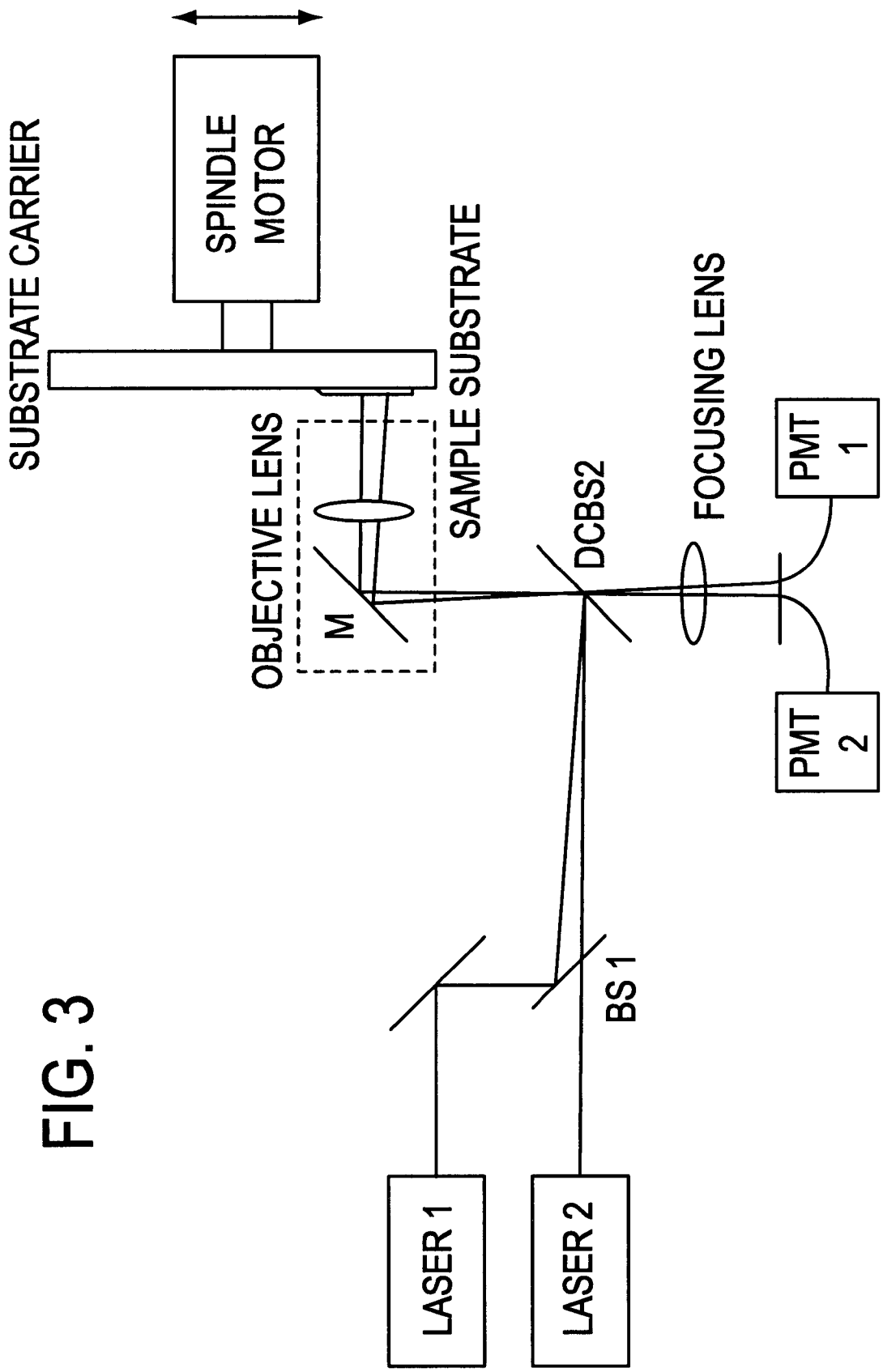
FIG. 3 depicts an alternative embodiment of the scanner illustrated in FIG. 1.

FIG. 3 shows an alternative design that differs from the one shown in FIG. 1 in the way the relative motion of sample and confocal scanning spots is achieved. The substrate is mounted eccentrically on a substrate carrier that is set into a spinning motion by a motor labeled as spindle motor here. The spindle carrier can be designed to carry more than one substrate in order to improve duty cycle. The spinning motion can be constant angular velocity or can be varied such that the linear velocity across the chip is independent of the radius of the scanning circle. (This radius may differ slightly for the two beams if they are offset other than tangentially, but this should typically only cause higher order effects.) While the spinning motion provides for a mostly tangential scanning motion, mostly radial scanning can be achieved by moving the motor with the substrate carrier e.g. using a translation stage. Preferably. the spinning motion would be the fast scanning motion and the translation the slow scanning motion such that the spots move across the substrate in a spiral trace. (A modification obvious to someone skilled in the art would be to slowly move the lens assembly radially in a way similar to it being moved quickly in FIG. 1.) In this case, a polarizer is introduced into each of the detection paths, the crosstalk between which is to be reduced by polarization. The polarizer is then oriented in such a way as to maximize transmission of the (partially) polarized emission to be detected in the channel in question. For an eccentric (rectangular) sample substrate the scanner will only receive signal intermittently. For a larger. concentric (round) substrate one would get a continuous signal while scanning an annular area on the substrate.

Figure 4:
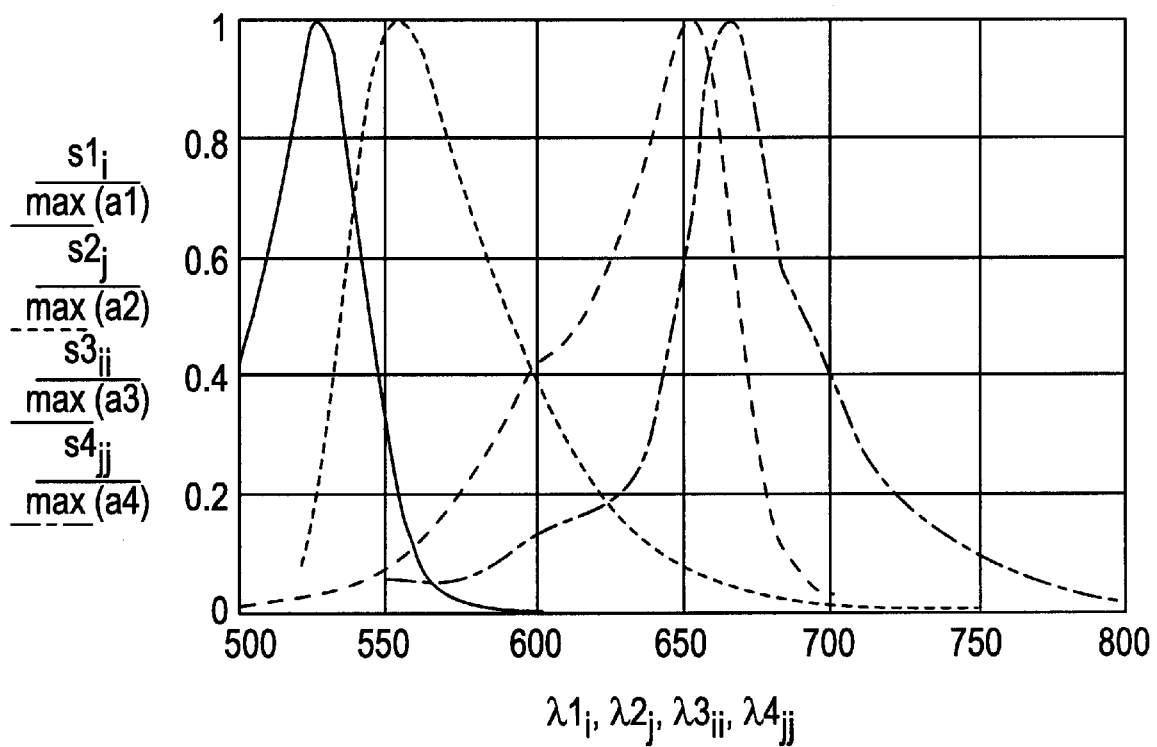
FIG. 4 depicts a graphical representation of the output from a typical set of lasers employed and the resulting emission from two dyes (R6G and Oxazine-1) scanned by the laser.

FIG. 4 illustrates the excitation frequencies of two laser beams and the resulting emission from a sample labeled with R6G and Oxazine dyes using the embodiment shown in FIG. 1: R6G is excited more than 10 times more efficiently by 532 nm radiation than by 633 nm radiation and for Oxazine the same is true for 633 nm with the two wavelengths swapped. Also, the emission spectra change for this mode of excitation with negligible emission occurring at wavelength shorter than the excitation wavelength. In an experiment with another pair of dyes (Cy3 and Cy5) a (geometric) mean crosstalk of about 0.1% was demonstrated.

The minimization of crosstalk between the dye emission channels is important as crosstalk will have an impact on low signal level measurements. For example, in a gene expression system that sees 10,000 photons in channel A, and 1 photon in channel B, let us consider 1% of crosstalk. Without crosstalk the Poisson noise in channel A would be 100 photons. and the noise in channel B would be 1 photon. With 1% of crosstalk, there is more than 10 photons of noise in channel B that result from the 100 crosstalk photons such that the noise in channel B is now equivalent to about 3.3 photons.

Although best results are obtained by the foregoing simultaneous multi-frequency scan of two or more separated spots on a sample labeled with two dyes. modifications of the invention, as set forth in the specifically described embodiments can be carried out without departing from the scope of the invention which is intended to be limited only by the scope of the appended claims. In particular while the preferred embodiment discloses the use of two lasers for generating two separate frequencies of light, it is possible to use a single laser and associated optics and filters to obtain two separate frequencies of light.

What is claimed is:

1. A multiple frequency laser induced fluorescence scanner for scanning a sample labeled with a plurality of luminescence dyes to cause fluorescence emission of light at different wavelengths, comprising:

at least one laser for forming a first and second beam of light of at least first and second predetermined excitation wavelengths, each excitation wavelength preferentially exciting one of the plurality of luminescence dyes;

an optical system for focusing the first and second beams of light on respective first and second spatially separated spots, and for collecting and transmitting the resulting emission through respective spatially separated apertures; and detector means coupled to the spatially separated apertures for measuring the emission signal level of the collected and transmitted emissions;

wherein the optical system further comprises focusing lenses and a pair of optical fibers that transmit the spectral emission from the focusing lenses to the detector, wherein the pair of optical fibers act as spatially separated apertures for the respective emissions from the spatially separated spots.

2. The multiple frequency laser induced fluorescence scanner as claimed in claim 1, the detector means further comprising at least two photomultiplier tubes for separately processing the emission of a sample labeled with two dyes.

3. The multiple frequency laser induced fluorescence scanner as claimed in claim 1, wherein the first and second beams of light are simultaneously focused on respective first and second separated spots by the same lens.

4. The multiple frequency laser induced fluorescence scanner as claimed in claim 1, the detector means further comprising filters for reducing the overlap of the emission spectra detected to minimize crosstalk.

5. A multiple frequency laser induced fluorescence scanner for scanning a sample labeled with a plurality of luminescence dyes to cause fluorescence emission of light at different wavelengths, comprising:

at least one laser for forming a first and second beam of light of at least first and second predetermined excitation wavelengths, each excitation wavelength preferentially exciting one of the plurality of luminescence dyes;

an optical system for focusing the first and second beams of light on respective first and second spatially separated spots, and for collecting and transmitting the resulting emission through respective spatially separated apertures; and detector means coupled to the spatially separated apertures for measuring the emission signal level of the collected and transmitted emissions; wherein the first and second beams focused on the spots have orthogonal polarizations;

the scanner additionally comprising polarizers each in a corresponding detection path.

6. A method for detecting fluorescence from a sample labeled with a plurality of fluorescent dyes, comprising:

generating a plurality of laser beams of a first and second wavelength;

directing the light of a first wavelength to a first spot and directing the light of a second wavelength to a second spot that is spatially separated from the first spot, to cause the sample to fluoresce and emit light at a plurality of different wavelengths; and scanning the spots across the sample in one direction and a slow scan direction;

applying the resulting emission from the dye-labeled sample to a detector to generate an output signal representative of the fluorescence from the sample, wherein each detector only receives light from a spatially defined area illuminated by the laser that preferentially excites the dye to preferentially be detected by that detector;

wherein a separation of the spots in the slow scan direction is provided to ensure that the excited dyes have fully recovered from any triplet saturation before they get scanned by the next laser beam.

7. The method for detecting fluorescence from a sample labeled with a plurality of fluorescent dyes as claimed in claim 6, the step of scanning more than one spot further comprising running the different laser beams through the same lens at a slightly different angle.

8. A method for detecting fluorescence from a sample labeled with a plurality of fluorescent dyes, comprising:

generating a plurality of laser light beams of a first and second wavelength;

directing light of the first wavelength to a first spot and directing light of a second wavelength to a second spot that is spatially separated from the first spot, to cause the sample to fluoresce and emit light at a plurality of different wavelengths;

scanning the spots across the sample;

applying the resulting emission from the dye-labeled sample to a detector to generate an output signal representative of the fluorescence from the sample, wherein crosstalk is minimized as the emission spectra of the dyes detected overlap as little as possible and each detector only receives light from a spatially defined area illuminated by the laser that preferentially excites the dye to preferentially be detected by that detector;

wherein the longest wavelength of the first and second wavelengths is scanned across the sample first.

9. The method according to claim 8 wherein the dyes comprise R6G and Oxazine-1.

10. The method according to claim 8 wherein the dyes comprise Cy3 and Cy5.

11. A method for detecting fluorescence from a sample labeled with a plurality of fluorescent dyes, comprising:

generating a plurality of laser beams of a first and second wavelength;

directing the light of a first wavelength to a first spot and directing the light of a second wavelength to a second spot that is spatially separated from the first spot, to cause the sample to fluoresce and emit light at a plurality of different wavelengths; and applying the resulting emission from the dye-labeled sample to a detector to generate an output signal representative of the fluorescence from the sample, wherein crosstalk is minimized as the emission spectra of the dyes detected overlap as little as possible and each detector only receives light from a spatially defined area illuminated by the laser that preferentially excites the dye to preferentially be detected by that detector;

wherein up to two dyes are excited with orthogonal polarizations of light, such that fluorescence that is polarized parallel to the excitation light which preferentially excites a given dye is detected in the absence of depolarization effects.

12. The method of claim 11, wherein the step of directing the light of a first wavelength and of a second wavelength, occurs simultaneously.

13. The method of claim 11 wherein the sample is a chip having different molecular counterparts in different areas of the chip which have hybridized.

* * * * *